(12) United States Patent
Fleischmann

(10) Patent No.: US 8,932,294 B2
(45) Date of Patent: Jan. 13, 2015

(54) ANTIMICROBIAL ELECTROSTATIC IMPLANTABLE MEDICAL DEVICE

(75) Inventor: David Fleischmann, Tempe, AZ (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 78 days.

(21) Appl. No.: 13/597,576

(22) Filed: Aug. 29, 2012

(65) Prior Publication Data

US 2013/0053903 A1    Feb. 28, 2013

Related U.S. Application Data

(60) Provisional application No. 61/528,914, filed on Aug. 30, 2011.

(51) Int. Cl.

| | |
|---|---|
| *A61B 17/58* | (2006.01) |
| *A61B 17/56* | (2006.01) |
| *A61F 2/30* | (2006.01) |
| *A61L 31/08* | (2006.01) |
| *A61L 31/16* | (2006.01) |
| *A61L 31/14* | (2006.01) |
| *A61B 17/68* | (2006.01) |

(52) U.S. Cl.
CPC ............... *A61L 31/088* (2013.01); *A61L 31/16* (2013.01); *A61L 31/14* (2013.01); *A61B 17/68* (2013.01); *A61L 2300/102* (2013.01); *A61L 2300/104* (2013.01); *A61L 2300/404* (2013.01)
USPC ............................. 606/62; 606/86 R; 606/76

(58) Field of Classification Search
USPC .................................................. 606/62, 86 R
See application file for complete search history.

(56) References Cited

U.S. PATENT DOCUMENTS

2006/0004431 A1\*    1/2006    Fuller et al. ................... 607/116

OTHER PUBLICATIONS

Naruse et al., Electrostatic micro power generation from low-frequency vibration such as human motion, Aug. 26, 2009, Journal of Micromechanics and Microengineering, 19.\*

\* cited by examiner

*Primary Examiner* — Andrew Yang
(74) *Attorney, Agent, or Firm* — Albert M. Churilla; Ning Yang

(57) ABSTRACT

A device and method for providing antimicrobial activity around a surgical implant. Antimicrobial activity is provided by the inclusion of a highly conductive material to a surgical implant and providing a low electrical charge to the implant. Electrical charge is provided by a static generator or battery attached to the implant or attached via electrical leads.

19 Claims, 2 Drawing Sheets

ANTIMICROBIAL ELECTROSTATIC IMPLANTABLE MEDICAL DEVICE

CROSS-REFERENCES TO RELATED APPLICATIONS

This application claims the benefit of U.S. Provisional Application No. 61/528,914, filed Aug. 30, 2011, which is incorporated by reference, herein.

BACKGROUND OF INVENTION

1. Field of Invention

The inventive subject matter relates to implantable medical devices with antimicrobial properties. The antimicrobial characteristics are afforded by inclusion of galvanically releasable material, possessing antimicrobial properties, and inducement of a static electrical charge.

2. Background Art

Materials are selected for inclusion into tissue implantable devices based on necessary strength, flexibility or rigidity, stability over time and their reactivity to tissue and physiological fluids. It is highly desirable to employ materials that evoke a minimal tissue response. Materials that have been found useful in endoprosthetic applications include cobalt chromium and molybdenum alloys and titanium and titanium alloys. Other, non-metallic materials have also been utilized, such as ceramic and carbon-based materials, as well as synthetic plastic, with some success. In all of these materials, an important characteristic is for the material not to be bioreactive (i.e., bioinert), durable and, in many cases, strong.

Another important consideration in implant surgery is infection control. The increased use of surgical implants, particularly in patients with compromised or reduced immune responses, makes control of infections in these patients a high priority (Darouiche, Clin. Infect. Dis., 33: 1567-72 (2001)). Infections associated with surgical implants are generally cumbersome to manage, have a significant impact of the quality of life of the patient and often result in prolonged hospital stays (Boxma, et al., Lancet, 347: 1133-1137 (1996); Whitehouse, et al., Infect. Control Hosp. Epidemiol., 23: 183-189 (2002)). Multiple approaches to controlling infection due to implants exist, including: irrigation of the surgical field; placement of an antimicrobial carrier near the wound site. However, more effective approaches at controlling infection following insertion of implants are desirable.

SUMMARY OF THE INVENTION

The current invention relates to a device and method of reducing antimicrobial growth around a surgical implant through generation of an electrical field. In a preferred embodiment, the method comprises coating endoprosthetic surgical implant device with a galvanically active metal or other substance, such as gold. An electric charge is applied to the device providing an electric charge on the endoprosthetic implant. The charge is supplied by a battery, either internally or externally located and connected, via wire leads, to the implant. In another embodiment, the charge is supplied by a static charge generator, which, in one embodiment, can be integral or part of the endoprosthetic device.

In another embodiment, the implant can be coated with antimicrobial compounds such as silver or antibiotics. In this embodiment, inhibition of microbial growth is achieved by both the release of silver ions, release being enhanced by the electrical charge, antibiotic and by the electrical charge itself.

In another embodiment, the static generator is a series of rotating discs or group of discs. As the discs rotate, an electrical charge accumulates on the discs, similar to that of a fan blade. Rotation of discs is mediated by the patient's movement. The discs are free to rotate in the same direction or, alternatively, rotate counter to each other. The disc assembly is electrically connected to an implant coated with a galvanically active substance, such as gold, either directly on the implant or via a wire connection to enable charge to flow from the charge generator to the galvanically active substance. The electrically charged metal coating enables electrons to flow freely through the implantable device reducing microbial growth and enhancing the anti-microbial properties of the metal coating.

In another embodiment, rather than discs, the device comprises sets of small plates, placed adjacent to each other positioned in different planes. Movement of the patient then causes the plates to move past each other, generating a static charge. An electrical field is then established between the coated silver.

The use of limited amounts of gold or other suitable substance, by coating the implant, enables the use of stronger metals, such as stainless steel for improved strength of the implant while avoiding connective tissue reaction and subperiosteal bone growth.

DETAILED DESCRIPTION OF PREFERRED EMBODIMENTS

Figure 1:
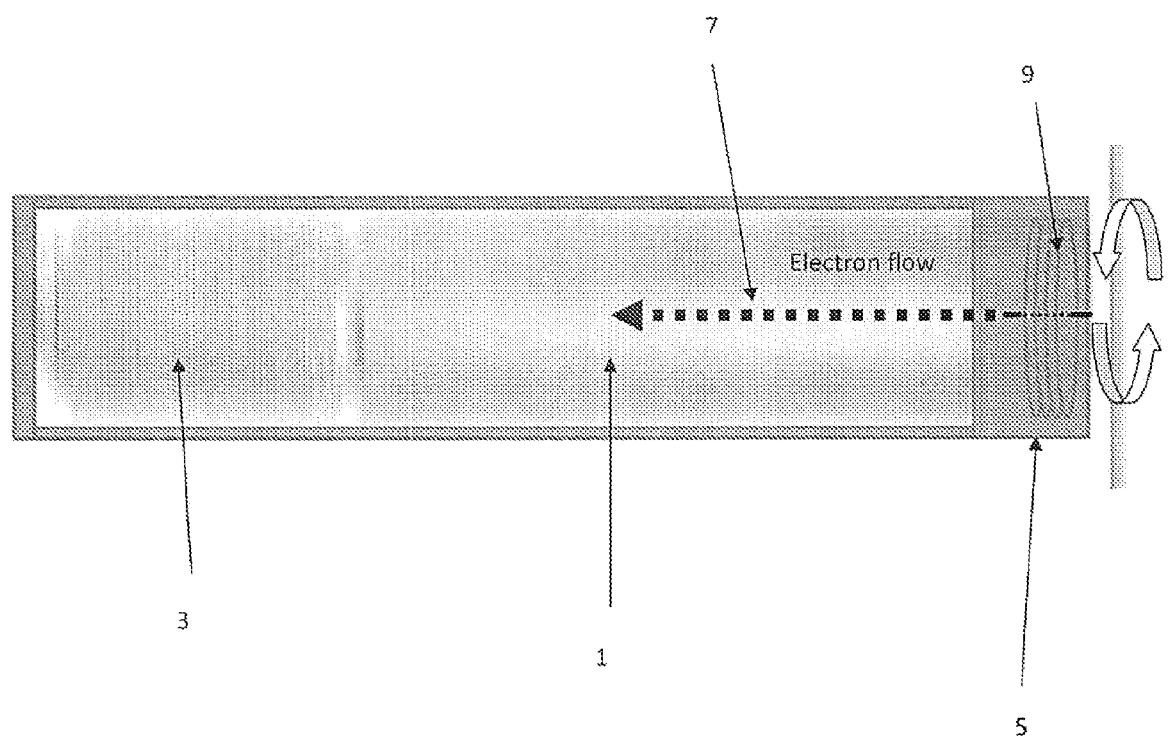
FIG. 1. Diagram of implant example (orthopedic pin) illustrating a cap region containing a static generator comprising circular discs.

Antimicrobial compounds refers to substances, which includes metal or metal salts or other compounds, that inhibit the growth of microorganisms, including bacteria. Static charge generator is a device capable of developing an electrical charge, by mechanical means as opposed to a battery. Endoprosthetic implant is a device to replace skeletal parts or portions of skeletal parts. This includes orthopedic pins or other implants designed to hold bones together. An implant is any device that is inserted into the body, such as an endoprosthetic implant.

The bactericidal properties of silver has been known for some time (Clement, and Jarrrett, Metal-based drugs 1: 467-482 (1994); Young, et al., Eur. J. Biochem., 116: 165-170 (1981); Masse, et al., J. Biomed. Mater. Res., 53: 600-4 (2000); Bodnar, E., J. Heart Valve Dis. 9: 170-173 (2000); Scales and Wilkinson, (U.S. Pat. No. 4,615,705); and Flick, (U.S. Pat. No. 6,087,549)). However, diffusion of silver ions from a metallic surface, such as silver foil, has been found to be low due to the low solubility in aqueous solutions.

In addition to the specific effects of silver as an anti-microbial agent, electric fields have also been suggested to have anti-microbial properties (Kermanshahi and Sailani, J. Microbiol. Immunol. Infect., 38: 394-398 (2005); Resenberg, et al., Nature 205: 698-699 (1965); Giladi, et al., Antimicrobial agents and chemotherapy, 52: 3517-3522 (2008)). However, effective means for effecting uniform electrical conductivity and maintenance of an electrical field on implants, such as an orthopedic pin, is problematic.

In a preferred embodiment, an orthopedic pin is capped on one end with a highly conductive material, such as gold, to improve electrical conductivity of the orthopedic pin. Application of small amounts of electrical current, by a battery or a static charge generator, is then applied to enabling electrons to flow to the gold capped pin to generate a uniform electrical charge over the implanted device.

A static generator, in this embodiment, is any device that generates an electrical charge. The static generator or battery can be external, such that electrical leads connected to the generator or battery are inserted through the skin and tissue and connected to the implant. Alternatively, the static generator or battery are also implanted, near the pin, and connected to the pin via leads or are integral and part of the implant.

Example 1

Antimicrobial Effect of Electrical Charge

As an example, an evaluation of the effect of static charge on bacterial growth inhibition was conducted. A stainless steel pin, capped at one end with a thin coating of gold, was centered into a petri dish containing a bacterial lawn. Static charge was provided to the gold capped end by a static charge generator comprising a wool fabric attached to spindle of a small electric motor, powered by a 9V battery. The wool, rotated by the motor, was abutted and rubbed against a plastic plate. Wires contacting the plastic plate lead to the gold capped stainless steel pin at the gold-capped end. The movement of the wool against the plate created a small electrical charge accumulation, which was carried to the pin. As a control, a stainless steel pin, with no gold cap, was also added to an identical petri dish containing a bacterial lawn, but where no electrical charge was applied.

After 48 hours, the distance from the ends of the pin to the beginning edge of bacterial growth was measured. The results showed that a clear ring of bacterial growth inhibition was evident around the pin. The greatest distance of bacterial growth inhibition was at the end of the pin that was gold capped, which was 15 mm further than the end that was not exposed to the charge. The pin in the plate that did not receive an electrical charge contained extensive bacterial colonies including adjacent to the pin. The control pin contained no evident zone of bacterial growth inhibition.

In another study, a stainless steel orthopedic pin and a stainless steel orthopedic pin containing a gold cap were centered in culture dishes (i.e., petri dishes) containing a bacterial lawn. A static charge, generated using a static plasma ball as a static charge generator, was applied, from the plasma ball to the stainless steel metal pin containing a gold cap. The estimated static electrical charge applied to the pin from the plasma ball generator was 0.25 pF. Colony formation was then observed in the petri dishes, the results of which are shown in Table 1.

As illustrated in Table 1, the number of colonies in the plate containing the gold-capped pin, with charge applied, was overall markedly reduced compared to the pin with no charge applied. The sharp reduction of colony count, from over 100 colonies per plate to under 10 colonies per plate, in the plates where charge is applied, is likely the result of charge dissipation into the culture media. Application of charge to the gold-capped pin resulted in no colonies growing within 10 mm to 18 mm from the pin. This was true even when charge was applied for only four hours.

TABLE 1

| Culture plate number | Pin Only | | Hours of applied static electricity (approx. 0.25 pF) Hours of applied static electricity (approx. 0.25 pF) | Pin plus static electricity plus gold cap | |
|---|---|---|---|---|---|
| | Distance of inhibition from pin (mm) | Colonies per plate (over 24 hour period) | | Distance of inhibition from pin (mm) | Colonies per plate (over 24 hour period) |
| 1 | 0 | >100 | 24 | 18 | 3 |
| 2 | 0 | >100 | 24 | 16 | 4 |
| 3 | 0 | >100 | 24 | 11 | 3 |
| 4 | 0 | >100 | 24 | 15 | 2 |
| 5 | 0 | >100 | 12 | 14 | 4 |
| 6 | 0 | >100 | 12 | 17 | 2 |
| 7 | 0 | >100 | 12 | 17 | 4 |
| 8 | 0 | >100 | 12 | 15 | 3 |
| 9 | 0 | >100 | 8 | 13 | 3 |
| 10 | 0 | >100 | 8 | 17 | 4 |
| 11 | 0 | >100 | 4 | 10 | 3 |

In the study, the reduction of colony formation was uniformly reduced throughout the dish containing the pin receiving the electrical charge. Since the reduction was uniform, and not centered or concentrated at one end of the pin or the other, including the gold containing end, the reduction in colonies was likely due to the increase in electrical conductivity of the pin afforded by the gold capping resulting in an electrical charge surrounding the pin. Collectively, these results suggest a barrier against bacterial infection can be obtained by the application of charge of four hours or less, coupled with a suitable charge acceptor.

Example 2

Antimicrobial Pin

The inventive device and method of its use incorporates an electric field in controlling infection following insertion of endoprosthetic implant, such as insertion of orthopedic pins. In one embodiment, the endoprosthetic implant is connected to a means for generating an electrical charge. In this embodiment, an electrically conductive material, such as gold, is coated onto various aspects of the endoprosthetic implant. In this embodiment, antimicrobial activity results from the presence of an electrical field produced from the charge distribution over the implant.

In another embodiment, if the pin also contains antimicrobial metal or compounds, such as silver. The release of silver ions are enhanced by the electrical current through iontophoresis, further improving the antimicrobial potential of the implant.

An important aspect of this invention is to enable the use of lower amounts conductive or antimicrobial coating material necessary to impede microbial growth. The use of limited amounts of conductive material such as gold and or antimicrobial material, such as silver, enables the use of stronger metals, such as stainless steel for improved strength of the implant, while avoiding connective tissue reaction and subperiosteal bone growth.

As an illustration, in one embodiment the static generator is caped onto the end of a surgical pin. An example of this configuration is illustrated in FIG. 1. In FIG. 1, the pin (1), which is typically constructed of stainless steel, comprises gold coating (3), or other highly conductive material, at one end or at multiple points along its length to act as an anode. In addition, other galvanically active substances can be used, including gold or iridium or alloys of silver. Antimicrobial materials can also be incorporated such as silver along the length of the pin. Discharge of silver ions, or other antimicrobial compounds incorporated along the pin, would then be enhanced by the electrical charge.

As illustrated in FIG. 1, at the other end of the pin is a cap (5), comprising a static generator (9). In FIG. 1, the static generator (9) is a series of rotating disc, which can either rotate in the same direction or in a direction counter to each other. Rotation of the discs creates a net negative electrical charge build-up on the discs due to deposition of electrons. The electrons, from the static generator (9) (i.e., discs) flow (7) from the cap (5) to the anode (3) (i.e., metal coatings), either through a direct connection through the implant or by movement of electrons through the tissue milieu, which has electrolytic characteristics, analogous to the flow of electrons in a battery. The use of gold or other highly conductive material, at specific points along the implant, as an anode, will serve to accept electrons created from the cap (5). The electron flow also serves to enhance discharge of silver ions, or other anti-microbial compounds, deposited along the pin. The use of limited amounts of highly conductive material and/or anti-microbial compounds, serves to reduce any medically deleterious effects associated with the metal and enable greater use of strengthening material in the construction of the implant.

Figure 2:
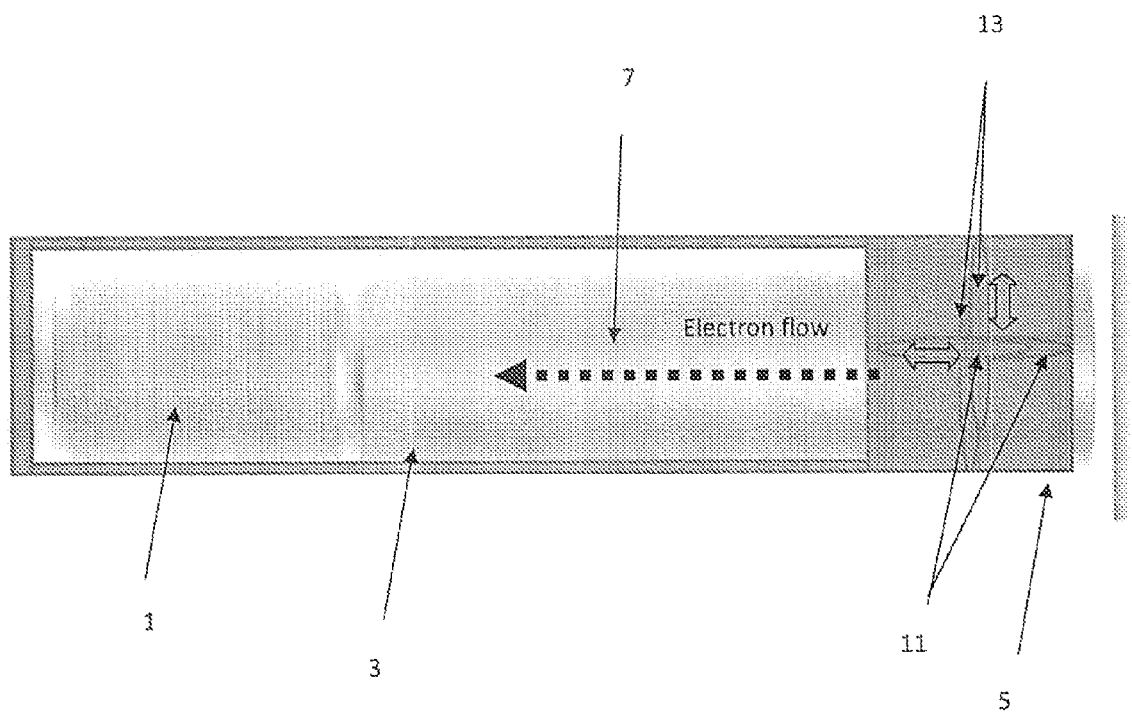
FIG. 2. Diagram of implant example (orthopedic pin) illustrating cap region containing a static generator comprising sliding plates.

In another illustration and embodiment, the cap (5) comprises a static generator comprising sets of small plates, rather than discs, which are positioned adjacent to other plates within the set. This is illustrated in FIG. 2. In this embodiment, sets of plates can be configured within the static generator to be oriented in different planes, such as horizontal (11) or vertical (13). Movement of the patient causes the plates to slide past the other plates within the set generating a static charge.

In another embodiment, as an alternative to a static charge generator, charge is supplied by either an implanted or externally located charge generator or other power source such as a battery system. In this embodiment, the cap (5) in FIG. 1 is replaced with either a battery or a connection, via electrical leads, to a battery or externally located electrical charge generator.

Example 3

Method of Reducing Microbial Growth Around an Implant

Reducing or eliminating microbial growth from a newly implanted implant, such as an orthopedic pin is critical. In a preferred embodiment, microbial growth in an implant is effected by inducing an electrical charge over the implant by coating a surgical implant, such as an orthopedic pin, with a highly conductive material, such as gold. The conductive material can be coated throughout the surface of the implant or only in specific locations. For example, in one embodiment, an orthopedic pin can be coated on one end of the pin. In the preferred embodiment, the implant, coated or capped with a conductive material, is electrically connected to a means for generating an electrical charge. The means for generating a charge can as a battery or a static charge generator.

In another embodiment, the method comprises reducing microbial growth by also coating the implant with an antimicrobial compound, such as silver or an antibiotic. In one embodiment, silver ion discharge is enhanced by the applied charge and compliments the antimicrobial activity of the applied charge and electrical field.

As an illustration, the implant, such as an orthopedic pin, can be coated with an antibiotic to initially control early infections surrounding the implant. Maintenance of antimicrobial growth, after the antibiotic is expended is through the electrical charge or through an electrical charge supplemented with coatings of other antimicrobial compounds such as silver with iontophoresis of silver ions.

What is claimed is:

1. A medical device comprising, a static generator for generating an electrical charge that is electrically connected to an endoprosthetic implant comprising a coating of a galvanic metal or compound so that electrical charge can flow over the surgical implant to the galvanic metal or compound, wherein said static generator comprises one or more, rotating, closely stacked discs.

2. The medical device of claim 1, wherein said means for generating an electrical charge is a battery.

3. The medical device of claim 1, wherein said means for generating an electrical charge is implanted inside the patient or located outside the patient and connected to the surgical implant via electrical leads or wires.

4. The medical device of claim 1, wherein said means for generating an electrical charge is part of the surgical implant.

5. The medical device of claim 1, wherein said means for generating an electrical charge comprises one or more sets plates, oriented in one or more planes, wherein each set comprises a pair of plates that are free to repeatedly slide past each other generating a static charge.

6. The medical device of claim 1, wherein said surgical implant is an orthopedic pin.

7. The medical device of claim 1, wherein said surgical implant contains an antimicrobial compound.

8. The medical device of claim 7, wherein said antimicrobial compound is silver.

9. A method of reducing microbial growth in an endoprosthetic implant comprising: coating a suitable endoprosthetic implant with a galvanic metal or other substance; and electrically connecting the implant to a means for generating an electrical charge.

10. The method of device of claim 9, wherein said galvanic metal is selected from the group consisting of silver, gold and iridium or an alloy of silver, gold or iridium.

11. The method of claim 9, wherein said implant is an orthopedic pin.

12. The method of claim 9, wherein said means for generating an electrical charge is a battery.

13. The method of claim 9, wherein said means for generating an electrical charge comprises one or more rotating, closely, stacked discs and wherein said rotation generates a static charge.

14. The method of claim 9, wherein said means for generating an electrical charge a pair of plates that are free to repeatedly slide past each other generating a static charge.

15. The method of claim 9, wherein said means for generating an electrical charge is implanted inside the patient or located outside the patient and connected to the surgical implant via electrical leads or wires.

16. The method of claim 9, wherein said implant contains an antimicrobial compound.

17. The method of claim 11, wherein said galvanic metal coats one end of said orthopedic pin.

18. The method of claim 16, wherein said antimicrobial compound is silver.

19. The method of claim 16, wherein said antimicrobial compound is an antibiotic.

\* \* \* \* \*